US012661382B2

(12) United States Patent
Magiatis et al.

(10) Patent No.: US 12,661,382 B2
(45) **Date of Patent: *Jun. 23, 2026**

(54) METHOD FOR OBTAINING OLEOCANTHAL TYPE SECOIRIDOIDS AND FOR PRODUCING RESPECTIVE PHARMACEUTICAL PREPARATIONS

(71) Applicant: OMPHAX SA, Ano Liosia (GR)

(72) Inventors: Prokopios Magiatis, Ampelakia Attikis (GR); Eleni Melliou, Ampelakia Attikis (GR); Panagiotis Diamantakos, Voula Attikis (GR); Aimilia Rigakou, Xirokampi Lakonias (GR)

(73) Assignee: OMPHAX SA, Ano Liosia (GR)

(*) Notice: Subject to any disclaimer, the term of this patent is extended or adjusted under 35 U.S.C. 154(b) by 836 days.

This patent is subject to a terminal disclaimer.

(21) Appl. No.: 17/430,547

(22) PCT Filed: Feb. 11, 2020

(86) PCT No.: PCT/GR2020/000015

§ 371 (c)(1),
(2) Date: Aug. 12, 2021

(87) PCT Pub. No.: WO2020/165614

PCT Pub. Date: Aug. 20, 2020

(65) Prior Publication Data

US 2022/0125869 A1 Apr. 28, 2022

(30) Foreign Application Priority Data

Feb. 13, 2019 (GR) .............................. 20190100077

(51) Int. Cl.
*A61K 36/63* (2006.01)
*A23L 33/105* (2016.01)
*B01D 11/04* (2006.01)

(52) U.S. Cl.
CPC ............ *A61K 36/63* (2013.01); *A23L 33/105* (2016.08); *B01D 11/0492* (2013.01); *A61K 2236/333* (2013.01)

(58) Field of Classification Search
CPC ................................ A61K 36/63; A01N 65/00
See application file for complete search history.

(56) References Cited

U.S. PATENT DOCUMENTS 3,288,824 A * 11/1966 Mahler .................... A61K 9/02
508/455

FOREIGN PATENT DOCUMENTS

JP 2009263295 A * 11/2009
JP 6 351124 7/2018
WO WO 2017/077134 5/2017
WO WO-2017077134 A1 * 5/2017
WO WO 2018/017967 1/2018

OTHER PUBLICATIONS

Ali Hashmi et al. (Traditional Uses, Phytochemistry, and Pharmacology of *Olea europae* (Olive), Evidence Based Complementary and Alternative Medicine, Jan. 25; vol. 2015, p. 1-29). (Year: 2015).*
Gullapalli and Mazzitelli (Polyethylene glycols in oral and parenteral formulations—A critical review, International Journal of Pharmaceutics 496 (2015) 219-239). (Year: 2015).*
Maria Rita Emma et. al. (Potential Uses of Olive Oil Secoiridoids for the Prevention and Treatment of Cancer: A Narrative Review of Preclinical Studies, International Journal of Molecular Sciences, 2021, 22, 1234) (Year: 2021).*
Antonio Procopio et al., "Synthethis, Biological Evaluation, and Molecular Modeling of Oleuropein and Its . . . ", Journal of Agr. & Food Chemistry, vol. 57, No. 63, Dec. 9, 2009.
Evangelos Katsoyannos et al., "Evaluation of the suitability of low hazard surfactants for the separation of . . . ", Journal of Separation Science, vol. 35, n.19, Aug. 9, 2012.
Loreta Kubiliene et al., "Alternative preparation of propolis extracts: comparison of their composition . . . ", BMC Compl. & Alternative Medicine . . . , vol. 15, No. 1, May 27, 2015.
Rita Limiroli et al., "1H and 13C NMR characterization of new oleuropein aglycones", Journal of the Chemical Society, Perkin Transactions 1, No. 12, Jan. 1, 1995.
Armandodoriano Bianco et al., "Biophenolic components of olives", Food Research International, vol. 33, No. 6, Jul. 1, 2000.
Milena Rizzo et al., "Antioxidant activity of oleuropein and semisynthetic acetyl-derivatives determined by . . . ", Pharma. & Clinical Research, vol. 69, No. 11, Sep. 6, 2017.

(Continued)

*Primary Examiner* — Anand U Desai
*Assistant Examiner* — Jacob A Boeckelman
(74) *Attorney, Agent, or Firm* — DP IP GROUP; Franco S. De Liguori

(57) ABSTRACT

The present invention relates to the method for obtaining in pure form or as a mixture of the bioactive diol forms of the main secoiridoid phenols present in olive oil and certain isomeric forms or derivatives thereof. Specifically, it relates to the production process of S-(E)-oleocanthadiol, S-(E)-oleaceinediol, 5S-(E)-oleomissionadiol, 5S-(E)-oleokoronadiol, oleuropeinediol and ligstrodiol and their corresponding polyethylene glycol hemiacetals through extraction of specifically selected olive oil with polyethylene glycol and then treated with water. It also relates to the pharmaceutical preparations containing the above substances in various combinations and the therapeutic properties of these preparations for the treatment of cancer, degenerative diseases of the central nervous system, diabetes, hyperlipidemia, inflammatory diseases and the prevention of creation of atherosclerotic plaques and thrombi.

9 Claims, 1 Drawing Sheet

(56) References Cited

OTHER PUBLICATIONS

Thielmann J. et al., "Antimicrobial activity of Olea europaeaLinne extracts and their applicability . . . ", Int. Journal of Food Microbiology, vol. 251, Mar. 28, 2017.

* cited by examiner

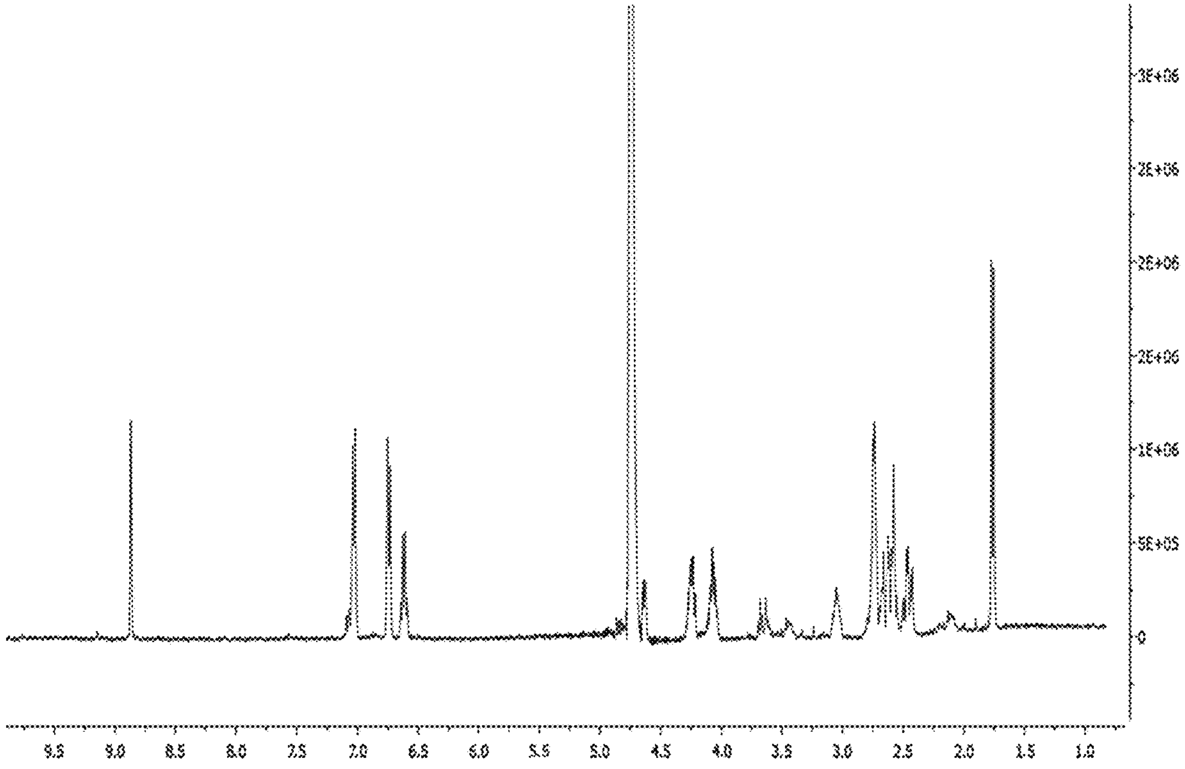
3E+06
2E+06
2E+06
2E+06
1E+06
5E+05
0
9.5
9.0
8.5
8.0
7.5
7.0
6.5
6.0
5.5
5.0
4.5
4.0
3.5
3.0
2.5
2.0
1.5
1.0

METHOD FOR OBTAINING OLEOCANTHAL TYPE SECOIRIDOIDS AND FOR PRODUCING RESPECTIVE PHARMACEUTICAL PREPARATIONS

FIELD OF ART

The application relates to a method for obtaining in pure form or as a mixture of the bioactive diol forms of the main secoiridoid phenols that are present in olive oil and certain isomeric forms or derivatives thereof, pharmaceutical preparations containing them and their therapeutic uses. The application relates to the field of medicine, pharmacy and food science.

STATE OF THE ART

Olive oil derived from the species *Olea europaea* L and all its subspecies and cultivars thereof contains secoiridoids of type I and/or II

I

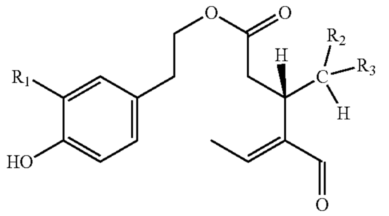

II

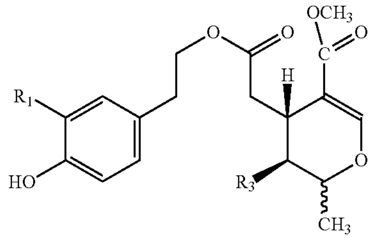

Wherein R1=H or OH, R2=H or $COOCH_3$, R3=CHO and the tautomers thereof.

More specifically, the secoiridoids of type I, S-(E)-oleocanthal (1) (R1-R2=H, R3=CHO), S-(E)-oleacein (2) (R1=OH, R2=H, R3=CHO), R/S-(E)-oleuropeinodial (3*a,b*) (R1=OH, R2=$COOCH_3$, R3=CHO) and R/S-(E)-ligstrodial (4*a,b*) (R1=H, R2=$COOCH_3$, R3=CHO) are the main phenolic substances found in most varieties of olive oil at concentrations ranging from 0 to 3000 mg/Kg (Journal of Agricultural and Food Chemistry 2014, 62(3), 600-607, OLIVAE 2015, 122, 22-35). The substances (3*a,b*) and (4*a,b*) are present in equilibrium with the tautomeric dialdehyde forms of S-(E)-oleomissional (3) and S-(E)-oleokoronal (4) and depending on the conditions they can be transformed to the monoaldehyde forms (5*a,b* and 6*a,b*) of general type II, which are present in olive oil usually in lower concentration.

For all substances (1-6) there are published methods of isolation from natural sources or methods of chemical synthesis as well as a number of published biological and pharmaceutical properties (anti-inflammatory, anti-cancer, anti-diabetic, neuroprotective, antioxidant).

However, the inventors, based on experiments they have carried out, are aware that these substances are not the true bioavailable active forms. In fact, substances (1-6) when they come into contact with human biological fluids, react chemically with water at a relatively slow rate, different for each substance, and are gradually converted to the active forms of S-(E)-oleocanthadiol (7), S-(E)-oleaceinediol (8), 5S-(E)-oleomissionadiol (9), 5S-(E)-oleokoronadiol (10) oleuropeinediol (11) and ligstrodiol (12) which exhibit increased activity and greatly increased water solubility with respect to substances (1-6).

It is therefore very important to develop methods allowing the production of substances (7-12) in pure or mixed form and pharmaceutical preparations or nutritional supplements or cosmetics which will contain the bioavailable forms (7-12) individually or In mixtures, thus not needing to be activated upon entering the human body. At the same time, it is very important to find new methods that will lead to the production of substances (1-6) or mixtures thereof at a higher yield than the existing methods and without using liquid chromatography to purify them.

To date, the structures of the substances (7, 8, 10, 11, 12) have never been fully and correctly eludicated spectroscopically nor has an industrially utilizable method of either selective production or In the form of a mixture been described. The spectroscopic data of the substance (9) has been described (J. Chem. Soc., Perkin trans. 1995, 1, 1519-1523) after enzymatic hydrolysis of pure oleuropein while substance (9) has been produced in very low yields, in mixtures with other substances that cannot be utilized, from olive fruit extracts (Food Res. Intl. 2000, 33:475-485).

It should be mentioned that there are references in the literature regarding the use of plants of the Phillyrea species, which have been used to produce the isomers of S—(Z)-oleaceinediol and S—(Z)-oleocanthadiol in mixture with other non-utilizable substances in very low yield (Phytochemistry Letters 8 (2014) 163-170). In addition, the isomeric substances S—(Z)-oleaceinediol, S—(Z)-oleocanthadiol, 5S-(Z)-oleomissionadiol and 5S-(Z)-oleokoronadiol appear to be produced in very low yields, in mixtures with other substances which cannot be utilized, when extracting olive oil with a mixture of water and methanol. (J. Agric. Food Chem. 2015, 66, 6053-6063.)

It is very important to note that substances (1-6) have different functional groups and in particular two aldehyde groups that each one of them can react with water in a different way and under different conditions (pH, temperature, time), the association of the specific structures (7-12) with specific therapeutic actions being therefore not obvious and having an inventive nature.

It should also be emphasized that there is a known method for producing the substance (1) described in WO2018017967 patent application which uses extraction of olive oil with water. This method relates to the production of aqueous nanoemulsion of substance (1) and not a true aqueous solution of substance (7) as described in the present invention. This is demonstrated by the relevant NMR spectrum in deuterated water (FIG. 1) where the almost complete elimination of the aldehyde group from position 3 can be observed. This point is a very significant difference from the international patent application WO2018017967 which uses a procedure similar to that mentioned in the present application but ultimately resulting in an emulsion of the oleocanthal aldehyde form (1) and not to the diol form (7).

There is also a patent FR2904312 (A1) 2008-02-01 in which olive oil is extracted with a water/alcohol mixture, but again there is no reference regarding the substances (7-12), their activity and the potential pharmaceutical use of the aqueous solution containing them.

Another Important element of innovation in the present invention is the use of polymeric hydrophilic alcohols immiscible with olive oil as an extractant. The proposed alcohols (polyethylene glycol of a size from PEG200 to PEG400) are biocompatible and may fully extract the target substances at a ratio of up to 1:100 (solvent:olive oil) as opposed to, for example, water requiring a ratio of 1:1. The present method has the advantage that the substances are extracted with a minimal amount of a biocompatible and non-toxic solvent which can then be mixed with water and release the diol forms (7-12) in the form of a true solution and it can simultaneously be incorporated as such in pharmaceutical preparations.

The solutions of substances (13-18) in polyethylene glycol, of a PEG200 to PEG400 size, in contrast to aqueous solutions or solutions of simple alcohols (e.g. methanol) used in the past for olive oil extraction, exhibit very high stability and allow for their utilization in the production of pharmaceutical preparations. This stage is particularly innovative compared to older extraction methods as the resulting solutions remain stable with no risk of hydrolysis, oxidation and polymerization for at least 12 months. It should also be pointed out that the previously mentioned use of methanol in the extraction of olive oil (J. Agric. Food Chem. 2015, 66, 6053-6063) makes it impossible to use the resulting solution for the production of pharmaceutical preparations for human use due to the toxicity of methanol.

Alternatively, instead of polyethylene glycol, ethanol or isopropanol may be used which lead respectively to ethyl or isopropyl hemiacetals of substances (1-6), which also release diol forms (7-12) upon contact with water.

The chemical structures of the substances described in the present invention are the following:

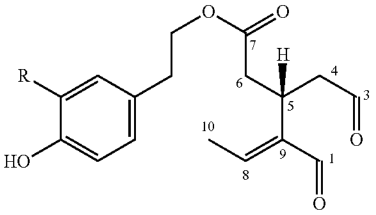

1: R = H
2: R = OH

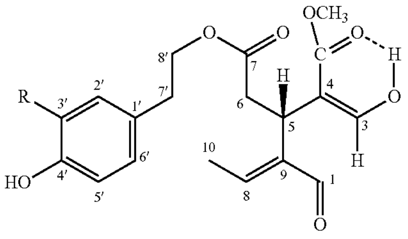

3: R = OH
4: R = H

-continued

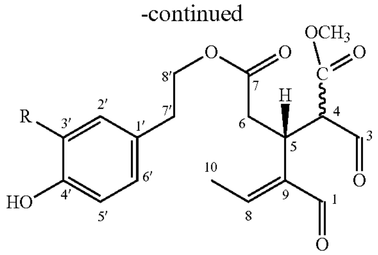

3a, b: R = OH
4a, b: R = H

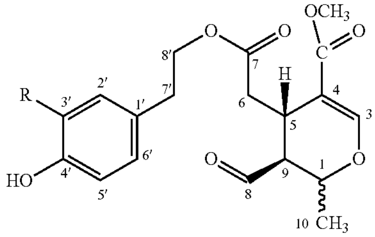

5a, b: R = OH
6a, b: R = H

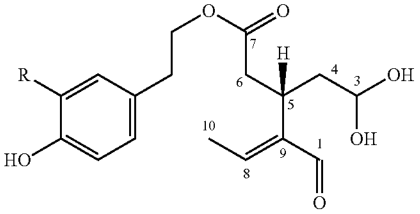

7: R = H
8: R = OH

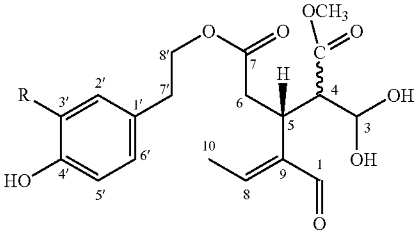

9: R = OH
10: R = H

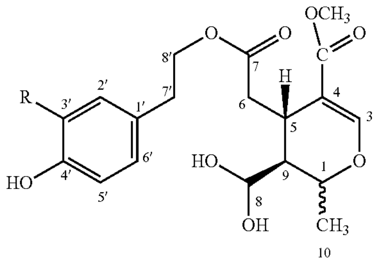

11: R = OH
12: R = H

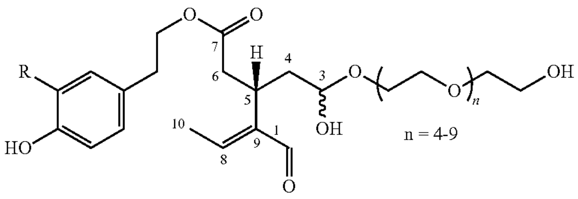

n = 4-9

13: R = H
14: R = OH

-continued

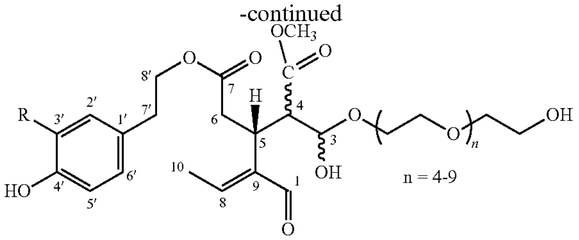

15: R = OH
16: R = H

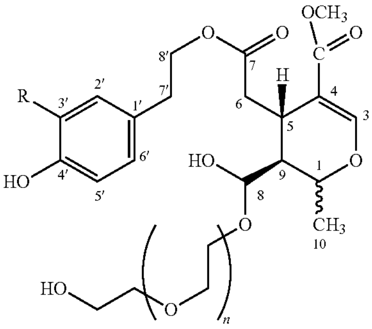

n= 4-9
17: R = OH
18: R = H

BRIEF DESCRIPTION OF THE DRAWING

FIG. 1 shows the $^1$H-NMR spectrum of oleocanthadiol (7) in deuterated water.

DETAILED DESCRIPTION OF PREFERRED EMBODIMENTS

Principle of the Method for Obtaining the S-(E)-Oleocanthadiol (7), S-(E)-Oleaceinediol (8), 5S-(E)-Oleomissionadiol (9), 5S-(E)-Oleokoronadiol (10), Oleuropeinediol (11) and Ligstrodiol (12) Substances or a Mixture of Whatever Thereof.

The Inventors based on experiments that they have performed they have found that substances (1-6) which are present in olive oil in lipophilic aldehydic form in variable concentrations, can react with hydrophilic polymeric alcohols of medium size, immiscible with olive oil and be transformed to polyethylene glycol hemiacetals (13-18) which can be selectively extracted and separated from the olive oil layer. In a next step, the polyethylene glycol hemiacetals after mixing with water can afford the diols (7-12).

According to an Illustrative Preferred Embodiment of the Invention, the Obtaining Method Comprises the Following Steps:

1a. Olive oil derived from *Olea europaea* L and all subspecies and cultivars thereof, containing substances (1-6) is mixed with polyethylene glycol (PEG 200 or PEG400) and stirred vigorously for a period of time ranging from 5 minutes to 24 hours at a ratio of 1 PEG:1 to 100 olive oil. The mixture is allowed to stand and the two phases are separated either by gravity or by centrifugation.

1b. The heavier layer containing the substances dissolved in the form of polyethylene glycol hemiacetal (13-18) is obtained and, if necessary, clarified by filtration to afford solution A1.

1c. Solution A1 is diluted with deionized and distilled water having pH=<7 at a ratio PEG:water=1:1 or 1:10 or 1:20 or 1:100 etc and the substances after at least 1 hour and for a maximum of 24 hours are fully converted to oleocanthadiol, oleaceinediol, oleomissionadiol, oleokoronadiol, oleuropeinediol and ligstrodiol. Any insoluble components are removed by filtration to afford solution B.

Solution A1 or B can be used for direct administration to human as an ingredient in medicinal products or food supplements or cosmetics with an aqueous carrier syrups, solutions, suspensions, or as an ingredient for injectable solutions or as an ingredient for transdermally administered products (incorporated in creams or gels) or as an ingredient in inhalation products.

1e. Solution A1 or B may be used, at an appropriate concentration, to prepare tablets following admixture with excipients (e.g., lactose), fluid bed drying and compression or suppositories following admixture with a suitable base. It should be noted that during the preparation of the tablets, using a suitable excipient and adjusting the moisture levels during drying allow the substance to remain in the diol form. This is confirmed by the instant dissolution of the tablet in water which would not have happened if the substance was in the lipophilic aldehyde form.

1f. Solution B passes through a column containing an adsorption resin (e.g. XAD4 or XAD16), the resin is washed up with a low boiling point organic solvent (<100° C.) miscible with water (e.g. methanol, ethanol or acetone) and the solution obtained is concentrated under reduced pressure providing the substances (1-6) (product C).

Specific case: in the case where the starting olive oil of step 1a is specifically selected to contain only one of the substances (1) or (2) or (3) or (4) or (5) or (6) and none of the other phenolic derivatives, then process 1*a* leads to step 1b where solution A1 contains the substance dissolved in the corresponding form of polyethylene glycol hemiacetal (13) or (14) or (15) or (16) or (17) or (18) and respectively in step 1c solution B contains the substance in the diol form (7) or (8) or (9) or (10) or (11) or (12). Accordingly, step 1f provides the substance (1) or (2) or (3) or (4) or (5) or (6) in pure form.

Pharmaceutical Properties of Oleocanthadiol (7), Oleaceinediol (a), Oleomissionadiol (9), Oleokoronadiol (10), Oleuropeinediol (11) and Ligstrodiol (12) or a Mixture Thereof.

1g. Solution A1 or B at an equimolar concentration of 0.5 μM showed potent antioxidant activity by inhibiting lipid peroxidation by 50%.

1h. Investigation of the cytotoxic activity of solution A1 or B showed that the mixture of oleocanthadiol (7), oleaceinediol (8), oleomissionadiol (9), oleokoronadiol (10), oleuropeinediol (11) and ligstrodiol (12) at equimolar concentration of 2.5 μM could induce cell death of 50% of HeLa and MCF-7 cancer cells and therefore solution A1 or B and any pharmaceutical preparations resulting from them can be used to treat cancer.

1i. Solution A1 or B at an equimolar concentration of 25 μM showed a 60% Inhibition of the COX-2 enzyme and therefore A1 or B solution and any pharmaceutical preparations thereof may be used to treat inflammatory diseases.

1j. By extension of cases 1g-1i, solutions A1 or B have the same therapeutic properties (neuroprotective, antidiabetic, antithrombotic) that are known for the substances (1-6) as in all cases at least partially they are converted to oleocanthadiol (7), oleaceinediol (8), oleomissionadiol (9), oleokoronadiol (10) oleuropeinediol (11) and ligstrodiol (12) in the aqueous medium in which the experiments to measure their biological activities are performed.

1k. Solution A1 or B containing substances (13-18) or (7-12) from 10% to 40% w/v showed that it could kill all microorganisms on the surface of a solid material acting as a sterilizer.

All of the above pharmaceutical preparations can be used with anti-cancer, cardioprotective, anti-inflammatory, anti-diabetic and neuroprotective properties.

Example 1

Olive oil (100 L) containing oleocanthal, oleacein, oleomissional, oleokoronal, oleuropein aglycon and ligtrosideaglycon in a total concentration of 1 g/kg, is mixed with PEG200 (1 L) and stirred vigorously for 10 minutes. The mixture is left to stand for 1 hour and the two layers are separated by gravity. The heavier layer is obtained and filtered to remove insoluble substances. The clear solution is diluted with deionized and distilled water having pH=<7 at a ratio PEG200:water=1:20 and the substances after 24 hours are converted to oleocanthadiol, oleaceinediol, oleomissionadiol, oleokoronadiol, oleuropeinediol and ligstrodiol. Any insoluble components are filtered off. The final solution has a total content of oleocanthadiol, oleaceinediol, oleomissionadiol, oleokoronadiol, oleuropeinediol and ligstrodiolin amounting to 5 g/Kg.

Example 2

Olive oil (100 L) containing 1 g/Kg of oleocanthal, which does not contain the other phenols 2-6, is mixed with PEG200 (1 L) and stirred vigorously for 10 minutes. The mixture is left to stand for 1 hour and the two layers are separated by gravity. The heavier layer is removed and filtered to remove insoluble substances. The clear solution is diluted with distilled water at a ratio of PEG200:water=1:10 and the substance is transformed into oleocanthadiol after 24 hours. Any insoluble components are removed by filtration. The final solution has an oleocanthadiol content of 10 g/L.

Example 3

The final solution of example 2 (5 ml) is mixed with a saturated sugar solution (95 ml) resulting to a syrup containing oleocanthadiol 50 mg/100 ml with anti-inflammatory activity.

Example 4

The polyethylene glycol solution of Example 1 (5 ml) is mixed with water (95 ml) and hydroxypropylcellulose (2 g) is added. The resulting gel has a total content of oleocanthadiol, oleaceinediol, oleomissionadiol, oleokoronadiol, oleuropeinediol and ligstrodiolin of 500 mg/100 mL and can be used for topical application in inflammatory diseases.

2. Principle of the Method for Obtaining S-(E)-Oleocanthadiol (7), S-(E)-Oleaceinediol (g), 5S-(E)-Oleomissionadiol (9), 5S-(E)-Oleokoronadiol (10), Oleuropeinediol (11) and Ligstrodiol (12) or a Mixture Thereof in Aqueous Solution According to Another Illustrative Preferred Embodiment of the invention, the Obtaining Method Comprises the Following Steps:

2*a*. Olive oil containing the substances (1-6) is mixed with deionized and distilled water having pH=<7 and stirred vigorously for a period of time ranging from 5 minutes to 24 hours at a ratio of 1 water:1 to 100 olive oil. The mixture is allowed to stand and the two phases are separated either by gravity or by centrifugation.

2b. The heavier layer is obtained and contains the substances oleocanthadiol (7), oleaceinediol (g), oleomissionadiol (9), oleokoronadiol (10), oleuropeinediol (11) and ligstrodiol (12) dissolved in water. The insoluble components are removed by filtration with a cellulose filter and the A2 solution is obtained.

2c. Solution A2 is concentrated by vacuum evaporation to the point of saturation at which the solution begins to get a milky form.

2d. If the evaporation from step 2c is continued until the water is completely evaporated or is lyophilized, a mixture of oleocanthal, oleacein, oleomissional, oleokoronal, oleuropein aglycon and ligstrosideaglycon (and their isomeric forms) will be obtained (product D).

2e. Solution A2 or the solution resulting from step 2c can be used for direct administration to human as an ingredient in pharmaceutical preparations or nutrition supplements or cosmetics in an aqueous carrier:syrups, solutions, suspensions, or as an ingredient in injectable solutions or as an ingredient in transdermally administered products (incorporated in creams or gels) or as an ingredient in inhalation products 2f. The solution from step 2c can be used at an appropriate concentration to prepare tablets after mixing with excipients (e.g. lactose), fluid bed drying and compression or suppositories after mixing with a suitable base.

Accordingly, all of the above pharmaceutical preparations can be used with anti-cancer, cardioprotective, anti-Inflammatory, anti-diabetic and neuroprotective properties.

Specific case: In the case where the starting olive oil of stage 2*a* is specifically selected to contain only one of the substances (1) or (2) or (3) or (4) or (5) or (6) and none of the other phenolic derivatives, then process 2*a* leads to step 2b where the aqueous solution contains every substance dissolved in the corresponding diol form (7) or (g) or (9) or (10) or (11) or (12) and respectively in step 2d the evaporation of the solution results in substances (1-6) with a purity of >95%.

Special Explanation:

It should be noted that the solutions obtained in steps 2b and 2c above are true solutions of the substances (7-12) in water and not emulsions of the aldehyde forms (1-6) in aqueous medium. This is evidenced by the corresponding NMR spectrum in deuterated water where the almost complete elimination of the aldehyde group from the position 3 of the substances (1-4) can be observed. This point is a very significant difference from the International patent application WO2018017967 which uses a procedure similar to that mentioned in Example 5 of this application but ultimately leads to an emulsion of the dialdehyde form of oleocanthal (1) and not the diol form (7).

Referring to FIG. 1 showing the $^1$H-NMR spectrum of oleocanthadiol (7) in deuterated water, it is shown to be a true solution of the diol form with a single aldehyde group (that has not reacted with water) and is not an emulsion of the dialdehyde form in water, which is present in a very small percentage.

Example 5

Olive oil (100 L) having a total concentration of oleocanthal, oleacein, oleomissional, oleokoronal, oleuropein aglycon and ligstrosideaglycon of 1 g/Kg is mixed with distilled and deionized water (100 L) having pH=<7, and stirred for 24 hours. The mixture is left to stand for 1 hour and the two layers are separated by gravity. The heavier layer is obtained and filtered to remove insoluble substances. The final solution has a total content of 500 mg/L of oleocanthadiol, oleaceinediol, oleomissionadiol, oleokoronadiol, oleuropeinediol and ligstrodiol.

Example 6

Olive oil (100 L) containing 1 g/Kg of oleocanthal, which does not contain the other phenols 24, is mixed with distilled and deionized water (100 L) and stirred mechanically for 24 hours. The mixture is left to stand for 24 hours and the two layers are separated by gravity. The heavier layer is collected and filtered to remove insoluble substances. The final solution has an oleocanthal content of 500 mg/L.

3. Principle of Method for Obtaining the Monoaldehyde Form of the Cyclic Aglycon of Oleuropein (5) and Ligstroside (6)

According to a Preferred Embodiment of the invention, the Method Consists of the Following Steps:

3*a*. If pH of the A2 or B aqueous solution containing oleomissionadiol (9) is adjusted to slightly alkaline (7.5-8) then the monoaldehyde form of the cyclic aglycon of oleuropein present in two isomeric forms (5*a*,*b*) is obtained upon evaporation. To remove any inorganic residues, the final product of the evaporation is dissolved in an organic solvent (e.g. dichloromethane or ethyl acetate), filtered and evaporated to yield product E.

3b. If the initial solution A2 or B contains oleokoronadiol (10) instead of oleomissionadiol (9) then the above procedure results in a pure monoaldehyde form of the cyclic aglycon of ligstroside in two isomeric forms (6*a*, *b*).

Example 7

Olive oil (10 L) containing 1 g/Kg of oleokoronal and none of the substances (1-3, 5, 6) is mixed with distilled water (100 L) and mechanically stirred for 24 hours. The mixture is left to stand for 24 hours and the two layers are separated by gravity. The heavier layer is collected and filtered to remove insoluble substances. The pH of the aqueous layer is adjusted to 7.6 and the solution is stirred for 24 hours, filtered and a solution of monoaldehyde cyclic aglycon of ligstroside is obtained. The solution is evaporated, the residue is redissolved in dichloromethane (500 ml), filtered and the solution is evaporated to yield the monoaldehyde form of the ligstroside cyclic aglycon (6*a*, *b*) (7 g) with a purity of >95%.

The invention claimed is:

1. Secoiridoids of type I and/or II

I

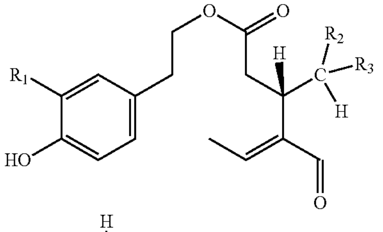

X1 =

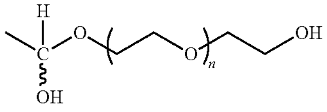

n = 4-9

-continued

II

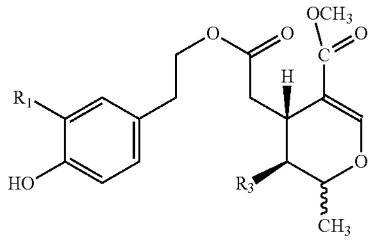

wherein

I: R1=H, R2=H or $COOCH_3$, R3=X1

II: R1=H or OH, R3=X1; and wherein the secoiridoids are pegylated with polyethylene glycol (PEG) having an average molecular weight from 200 to 400, at a PEG-to-secoiridoid ratio ranging from 1:1 to 100:1.

2. Secoiridoids of type I and/or II

I

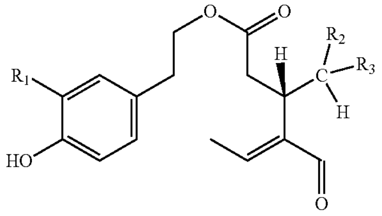

X1 =

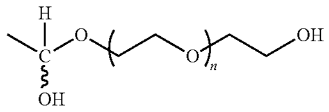

n = 4-9

II

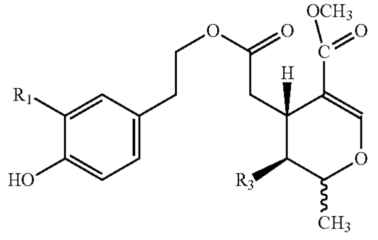

wherein

I: R1=H, R2=H or $COOCH_3$, R3=X1

II: R1=H or OH, R3=X1 individually or in any combination thereof, the secoiridoids being pegylated with polyethylene glycol (PEG) having an average molecular weight from 200 to 400, at a PEG-to-secoiridoid ratio ranging from 1:1 to 100:1, for the production of pharmaceutical preparations for oral or transdermal administration or injectable solutions or suppositories or tablets produced after drying and compression.

3. Secoiridoids of type I and/or II

I

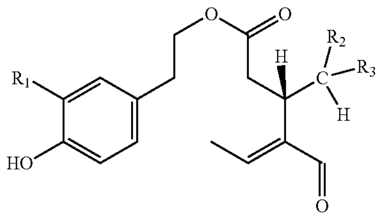

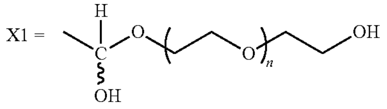

n = 4-9

II

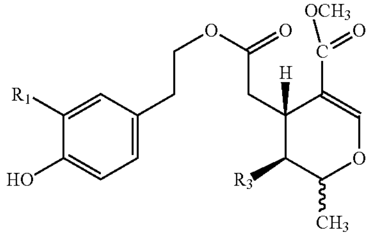

wherein

I: R1=H, R2=H or $COOCH_3$, R3=X1,

II: R1=H or OH, R3=X1, the secoiridoids being pegylated with polyethylene glycol (PEG) having an average molecular weight from 200 to 400, at a PEG-to-secoiridoid ratio ranging from 1:1 to 100:1, for the manufacture of nutritional supplements.

4. A pharmaceutical preparation containing the secoiridoids of claim 2 for the treatment of cancer, and inflammatory diseases, and for preventing the creation of atherosclerotic plaques and thrombi, wherein the pharmaceutical preparation is administered at a dose ranging from 1 mg to 1000 mg.

5. Secoiridoids of type I and/or II

I

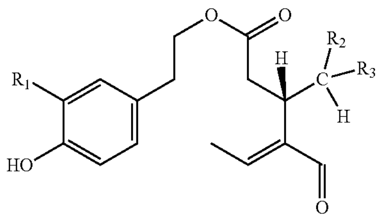

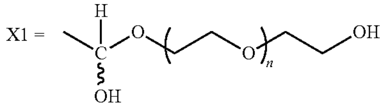

n = 4-9

-continued

II

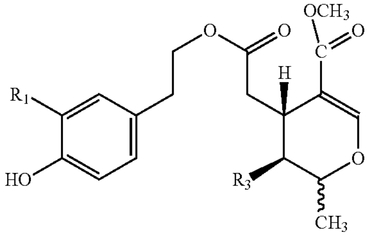

wherein

I: R1=H, R2=H or $COOCH_3$, R3=X1

II: R1=H or OH, R3=X1, the secoiridoids being pegylated with polyethylene glycol (PEG) having an average molecular weight from 200 to 400, at a PEG-to-secoiridoid ratio ranging from 1:1 to 100:1, for the preparation of solutions to sterilize solid materials.

6. A pharmaceutical preparation containing the secoiridoids of claim 2, wherein the secoiridoids are obtained from olive oil of the species *Olea europaea* L or any of its subspecies and cultivars, containing secoiridoids of type I and/or II with R1=H or OH, R2=H or COOCH3, R3=CHO and their tautomers, either in individual form or in any combination thereof; and wherein the olive oil is mixed with the polyethylene glycol (PEG) having an average molecular weight from 200 to 400, at a PEG:olive oil ratio ranging from 1:1 to 1:100.

7. A pharmaceutical preparation containing the secoiridoids of claim 3, wherein the secoiridoids are obtained from olive oil of the species *Olea europaea* L or any of its subspecies and cultivars, containing secoiridoids of type I and/or II with R1=H or OH, R2=H or COOCH3, R3=CHO and their tautomers, either in individual form or in any combination thereof; and wherein the olive oil is mixed with the polyethylene glycol (PEG) having an average molecular weight from 200 to 400, at a PEG:olive oil ratio ranging from 1:1 to 1:100.

8. A pharmaceutical preparation containing the secoiridoids of claim 1, wherein the secoiridoids are obtained from olive oil of the species *Olea europaea* L or any of its subspecies and cultivars, containing secoiridoids of type I and/or II with R1=H or OH, R2=H or COOCH3, R3=CHO and their tautomers, either in individual form or in any combination thereof; and wherein the olive oil is mixed with the polyethylene glycol (PEG) having an average molecular weight from 200 to 400, at a PEG:olive oil ratio ranging from 1:1 to 1:100.

9. A pharmaceutical preparation containing the secoiridoids of claim 5, wherein the secoiridoids are obtained from olive oil of the species *Olea europaea* L or any of its subspecies and cultivars, containing secoiridoids of type I and/or II with R1=H or OH, R2=H or COOCH3, R3=CHO and their tautomers, either in individual form or in any combination thereof; and wherein the olive oil is mixed with the polyethylene glycol (PEG) having an average molecular weight from 200 to 400, at a PEG:olive oil ratio ranging from 1:1 to 1:100.

* * * * *